United States Patent
Neef et al.

(10) Patent No.: US 10,151,673 B2
(45) Date of Patent: Dec. 11, 2018

(54) TREATMENT DEVICE FOR TREATING HISTOLOGICAL OR CYTOLOGICAL SAMPLES

(71) Applicant: LEICA BIOSYSTEMS NUSSLOCH GMBH, Nussloch (DE)

(72) Inventors: Bernhard Neef, Nussloch (DE); Markus Wittmann, Heidelberg (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 0 days.

(21) Appl. No.: 15/629,822

(22) Filed: Jun. 22, 2017

(65) Prior Publication Data
US 2018/0003600 A1    Jan. 4, 2018

(30) Foreign Application Priority Data
Jun. 30, 2016 (DE) .......... 10 2016 111 991

(51) Int. Cl.
*G01N 1/00* (2006.01)
*G01N 1/31* (2006.01)
(Continued)

(52) U.S. Cl.
CPC ......... *G01N 1/31* (2013.01); *G01N 35/00663* (2013.01); *G01N 35/00732* (2013.01);
(Continued)

(58) Field of Classification Search
CPC ..................................................... G01N 1/00
See application file for complete search history.

(56) References Cited

U.S. PATENT DOCUMENTS 7,749,441 B2 * 7/2010 Hanawa ............. G01N 35/1002
422/63
8,158,058 B2 * 4/2012 Shiba ............... G01N 35/00663
422/63
(Continued)

FOREIGN PATENT DOCUMENTS

DE    102012216330 A1    3/2014

OTHER PUBLICATIONS

Leica Biosystems, Leica ST5020 Multistainer and Leica CV5030 Glass Coverslipper Brochure (Jul. 2004).
(Continued)

*Primary Examiner* — Jyoti Nagpaul
(74) *Attorney, Agent, or Firm* — Hodgson Russ LLP (57) ABSTRACT

A treatment device (1) for treating histological or cytological samples has a plurality of containers (6) for different treatment agents and a detection apparatus (2) for detecting a code which unequivocally identifies a type of a treatment agent or a type of a group of treatment agents from a package or replacement container of a treatment agent or group of treatment agents. The device furthermore has an evaluation apparatus (18) that, based on a detected code, ascertains which of the containers is or are to be replenished or replaced, and an indicating apparatus (4) which communicates to a user the ascertained container (6) or containers (6) that is or are to be replenished or replaced. The indicating apparatus may include a display (5) presenting a schematic image of the plurality of containers (6) with image(s) of each ascertained container being marked, and/or a light source (15) that illuminates each ascertained container.

18 Claims, 6 Drawing Sheets

(51) Int. Cl.
*G01N 35/00* (2006.01)
*G01N 35/10* (2006.01)

(52) U.S. Cl.
CPC ... *G01N 35/00871* (2013.01); *G01N 35/1002* (2013.01); *G01N 2035/00673* (2013.01); *G01N 2035/00811* (2013.01); *G01N 2035/00821* (2013.01); *G01N 2035/00881* (2013.01); *G01N 2035/00891* (2013.01)

(56) References Cited

U.S. PATENT DOCUMENTS

| | | | |
|---|---|---|---|
| 8,455,256 B2 * | 6/2013 | Yamato | G01N 35/026 422/63 |
| 8,840,848 B2 | 9/2014 | Kraihanzel | |
| 2002/0018733 A1 | 2/2002 | Kapplein et al. | |
| 2002/0090730 A1 | 7/2002 | Eckert et al. | |
| 2002/0090731 A1 | 7/2002 | Gropp et al. | |
| 2005/0205673 A1 | 9/2005 | Morris et al. | |
| 2008/0199955 A1 | 8/2008 | Ulbrich et al. | |
| 2009/0017491 A1 | 1/2009 | Lemme et al. | |
| 2012/0129247 A1 | 5/2012 | Tanoshima et al. | |
| 2016/0377515 A1 | 12/2016 | Berberich | |

OTHER PUBLICATIONS

Leica Biosystems, Surgipath Consumables Product Range Brochure (Aug. 2012).
Leica Biosystems, Leica ASP300 The Advanced Smart Tissue Processor Brochure (Apr. 2001).
Leica Biosystems, Leica ST5020 Multistrainer Operating Instructions (Aug. 2009).
Beckman Coulter PK7300 Automated Microplate System Brochure (2009).
Beckman Coulter, Flow Cytrometry Catalog (2016).
Beckman Coulter, UniCel DxC 660i Synchron Access System Datasheet (2009).
Hanna et al., Bar Coding and Tracking in Pathology, 8 Surgical Pathology 123 (Feb. 17, 2015).
Equipar S.A., Multiparameter Bioanalytical System (2004).
Joseph Burns, RFID Lab Inventory System Saves $465k in First Year, The Dark Report (Jun. 1, 2015).
European Directorate for the Quality of Medicines & Health Care, OMCL Network of the Councel of Europe Quality Management Document PA/PH/OMCL (11) 157 5R (May 1, 2012).
Instrumentation Laboratory, ACLTOP750 LAS Datasheet (2015).
Andrzej Knafel et al., Clinical Laboratory Automation, Health Level Seven (2003).

* cited by examiner

TREATMENT DEVICE FOR TREATING HISTOLOGICAL OR CYTOLOGICAL SAMPLES

CROSS-REFERENCE TO RELATED APPLICATIONS

The present application claims priority of German patent application no. 10 2016 111 991.1 filed Jun. 30, 2016, the entire disclosure of which is incorporated herein by reference.

FIELD OF THE INVENTION

The invention relates to a treatment device for treating histological or cytological samples, which comprises a plurality of containers for different treatment agents.

The invention furthermore relates to a treatment agent product that contains at least one treatment agent or a group of treatment agents.

BACKGROUND OF THE INVENTION

Treatment devices, in particular automated treatment devices, for example tissue processors or automatic stainers, are often used for the treatment of histological or cytological samples. These treatment devices usually contain a plurality of containers in which the different treatment agents, usually chemically effective liquids, that are required for the individual treatment steps are located. The samples are usually automatically introduced successively into the containers by suitable handling apparatuses.

There are also processors that comprise only a single container into which the samples to be treated are introduced. The treatment agents provided for the respective pending treatment step are automatically placed into that container, and removed again after the respective treatment step.

The treatment agents must be regularly replaced or replenished, because they are consumed and/or because they have only a limited working life.

With processors in particular it is usual to use containers, in particular system containers, that are standardized in terms of their shape and size, and to replace them as necessary with replacement containers of the same shape and size having fresh treatment agent. System containers that can be replenished as necessary can additionally be installed in processors.

With automatic stainers, the containers are usually replenished or refilled when the respective staining chemical falls below a minimum fill level or is no longer usable. Groups of staining agents, called "staining kits," that contain several individual chemicals are often used, each of the individual chemicals needing to be introduced into a separate container of the automatic stainer. In most automatic stainers, staining can be performed without difficulty using the treatment agents of different staining kits. In this context, an automatic stainer of this kind can comprise containers in which the treatment agents of a first staining kit are located, while the treatment agents of a second staining kit are located in other containers.

DE 100 10 140 A1 discloses an apparatus for preferably automatic handling and/or processing of specimens, in particular in the field of medical technology. The apparatus comprises at least a processing station and a sample carrier for conveying a specimen to the processing station, through the processing station, and away from the processing station. The sample carrier has a code with which information about the specimen and/or about the handling or processing of the specimen can be associated, the information being readable or retrievable via the code.

DE 10 2007 008 713 A1 discloses a tissue infiltration apparatus for samples located in cassettes. The tissue infiltration apparatus encompasses at least two liquid containers and a transport apparatus. A liquid having a predefinable property can be introduced into the liquid container. The transport apparatus is embodied in such a way that with it, at least two transport baskets are transportable within the tissue infiltration apparatus. With the transport apparatus, a transport basket can be conveyed to a liquid container or moved away from a liquid container. It is possible to predefine an execution sequence in which the transport baskets pass through the liquid containers of the tissue infiltration apparatus. The transport baskets, or the cassettes transported therewith, can comprise a barcode or a machine-readable imprint or a transponder, so that the whereabouts within the tissue infiltration apparatus of a cassette having the specimen arranged therein, or of a transport basket, can be ascertained therewith.

DE 100 52 834 A1 discloses a method for treating specimens, in particular cytological or histological prepared specimens, for example in an automatic stainer. In the method, the specimens are conveyed by means of a transport device, preferably on sample carriers and in sample carrier magazines, to various processing stations, inserted thereinto, and treated in accordance with a selectable or predefinable or programmable treatment program. For this, there is an unequivocal association of the sample carriers or sample carrier magazines, or clips or labeling fields to be applied thereonto, with specific treatment programs.

DE 100 52 833 A1 discloses a method for treating specimens, in particular cytological or histological prepared specimens, for example in an automatic stainer, in which the specimens are conveyed by means of a transport device, preferably on sample carriers and in sample carrier magazines, to various processing stations, inserted thereinto, and treated in accordance with a predefinable treatment program. Automatic monitoring of the reagents occurs, predefinable parameters being considered in the monitoring. Those parameters relate, for example, to working life limits or to physical composition.

DE 10 2012 216 336 A1 discloses an automatic stainer for staining, in particular hematoxylin-eosin (H & E) staining, of a histological sample, which exposes the sample to the action of at least one staining agent with application of at least one staining parameter. The automatic stainer comprises an input means with which a staining parameter is definable, in particular is inputtable or is selectable from a plurality of possible staining parameters. The automatic stainer furthermore comprises a control apparatus that, upon application of the defined staining parameter, ascertains the predicted expected result of an action and indicates it to the user with an indicating apparatus, although the automatic stainer does not actually stain the sample. The properties of a staining kit can be communicated to the automatic stainer by automatic readout of a barcode or an RFID chip arranged on the supplier packaging of the staining kit, and taken into consideration by the control apparatus.

DE 10 2012 216 330 A1 discloses a method for processing a histological sample, in which method the histological sample is acted upon with the application at least one processing parameter. A processing parameter is defined, and the predicted expected result upon application of the defined processing parameter is ascertained and indicated, although the sample is not actually modified in that context.

SUMMARY OF THE INVENTION

The object of the present invention is to describe a treatment device in which the replacement or topping up of treatment agents is simplified, and the risk of incorrect replacement or topping up of treatment agents is reduced.

The object is achieved by a treatment device which is characterized by a. a detection apparatus (2) for detecting a code, which characterizes in unequivocally identifiable fashion the type of a treatment agent, from a package or from a replacement container of a treatment agent, b. an evaluation apparatus (18) that, in consideration of a detected code, ascertains which container (6) having the treatment agent for whose package the code was detected is to be replenished, or which container (6) is to be replaced with a replacement container having treatment agent the code of which, or of whose package, was detected, c. an indicating apparatus (4) that communicates to the user the ascertained container (6) that is to be replenished or replaced.

According to an alternative inventive idea, the object is achieved by a treatment device which is characterized by a. a detection apparatus (2) for detecting a code, which characterizes in unequivocally identifiable fashion the type of a group of treatment agents, from a package or from a replacement container of a group of treatment agents, b. an evaluation apparatus (18) that, in consideration of the detected code, ascertains which of the containers (6) having which of the group of treatment agents whose code was detected is to be replenished, or which container (6) is to be replaced with which replacement container of the group of treatment agents whose code was detected, c. an indicating apparatus (4) that communicates to the user which of the ascertained containers (6) having which of the group of treatment agents whose code was detected is to be replenished, or which of the ascertained containers (6) is to be replaced with which replacement container of the group of treatment agents whose code was detected.

It has been recognized that complications can occur at times when topping up or replacing the containers of treatment devices for treating histological or cytological samples. It can happen in this context, in particular, that a treatment agent is inadvertently introduced into the wrong container or that the inadvertently wrong container of the treatment device is replaced with a replacement container. This has to do in particular with the fact that a treatment device, for example an automatic stainer, can comprise 50 or more containers, so that good clarity usually does not exist.

Replenishment of a container with the wrong treatment agent, or replacement of a container with a replacement container having the wrong treatment agent, is usually not noticed until the samples inadvertently treated with the wrong treatment agent do not exhibit the desired nature and/or properties after treatment. Often the samples are unavailable for further investigation.

With the treatment device according to the present invention, the risk of replenishing or replacing the wrong container is advantageously very considerably reduced, in particular because the user is concretely informed by means of an indicating apparatus by way of indirect or direct indications, very specifically for the treatment agent currently to be replenished or replaced, as to the respective correct container for replenishment or replacement. The risk of inadvertent confusion in everyday routine operation is thereby eliminated or at least very considerably reduced.

The treatment device according to the present invention comprises a detection apparatus for detecting a code that characterizes in unequivocally identifiable fashion the type of a treatment agent or the type of a group of treatment agents, for example of a staining kit.

The detection apparatus can be configured, for example, to detect a code optically. For example, the detection apparatus can be configured as a barcode reading device or a reading device for a QR code. It is also possible, for example, for the detection apparatus to be configured to read a machine-readable imprint from the package of a treatment agent or from a container of a treatment agent.

Alternatively or additionally, provision can also be made that the detection apparatus is configured to detect a transponder code, for example an RFID transponder code. Provision can advantageously be made for this purpose that a transponder which contains the code is arranged on a package of one or more containers or on a replacement container, and that the detection apparatus is configured to read out the code, in particular in non-contact fashion.

It is important in principle to detect unequivocally, via the code, the type of the treatment agent to be replaced or to be used for replenishment, in order to be able to define reliably the container of the treatment agent into which the treatment agent is to be introduced, or which container of the treatment agent is to be replaced with the replacement container whose code was read in. What is meant in this regard by the term "type" is not only a general class or species of different reagents, at least if the relevant container of the treatment device is not thereby unequivocally identifiable.

The term "type" instead means in particular a concrete indication (or several indications) that permits the correct container of the treatment device for replenishment or replacement to be unequivocally associated. Such an indication can be in particular an information item regarding the manufacturer and/or a product number and/or a chemical composition, in particular a chemical structural formula. The term "type" can thus be understood as a designation for a species of treatment agents only if that is sufficient to unequivocally and reliably identify the corresponding container of the treatment device for replenishment or replacement.

In an advantageous embodiment, the evaluation apparatus comprises a memory in which, in particular, which type of treatment agent is located in which of the containers of the treatment device is stored or storable. Very generally, the evaluation apparatus can comprise a memory in which associations of containers with types of treatment agents are stored and/or storable. In particular, the age of the respective treatment agent and/or the current fill level can additionally be stored in container-specific fashion. In particular, provision can advantageously be made that the evaluation apparatus takes the data stored in the memory into consideration when ascertaining which container is to be replaced or replenished.

Alternatively or additionally, provision can be made that a separate treatment agent identifier is associated with each of a plurality of types of treatment agents, and those associations are stored in the memory. In such a database it is possible, for example, to detect and associate with a treatment agent identifier the treatment agents that are usable in a treatment device of the present kind and/or are usually used in a treatment device of the present kind or are commercially common.

In particular, provision can advantageously be made that a separate treatment agent identifier is associated with each type of treatment agent that is present in at least one of the containers of the treatment device, and those associations are stored in the memory. In addition, in particular, a container identifier can furthermore be associated with each treatment agent identifier of a treatment agent present in a container of the treatment agent, and the association can be stored in the memory.

For example, provision can advantageously be made that firstly a code is detected by means of the detection apparatus; and that the evaluation apparatus then associates with the detected code a treatment agent identifier from a plurality of previously stored treatment agent identifiers. If an unequivocal association happens not to be possible, for example a warning message is outputted, or preferably the user is prompted to input further information, in particular by means of the detection apparatus, regarding the treatment agent or the group of treatment agents.

After a successful association of the detected code with a treatment agent identifier, the evaluation apparatus can advantageously, in a further step, read out from the memory, on the basis of the treatment agent identifier, the container identifier of that container which contains the type of treatment agent corresponding to the treatment agent identifier. Based on the container identifier, in a further step the user can be informed by means of the indicating apparatus as to the container that is to be replenished or replaced.

The procedure can be analogous if the detected code relates to a group of treatment agents, for example a staining kit; here, analogously, several treatment agent identifiers need to be ascertained, and several associations with container identifiers read out. Provision can be made for this purpose, in particular, that associations of codes with several treatment agent identifiers are stored in the memory, each code relating to a group of treatment agents. For example, the group of treatment agents can be detected and respectively associated with treatment agent identifiers that are usable in a treatment device of the present kind and/or are usually used in a treatment device of the present kind or are commercially usual.

In a particular embodiment of the treatment device according to the present invention, provision can be made that among the plurality of containers, several containers for the same treatment agent are present. A treatment device of this kind is suitable in particular for allowing several samples or several groups of samples to be treated simultaneously and mutually independently with the same treatment agents.

With such an embodiment of a treatment device according to the present invention, provision can advantageously be made that the evaluation apparatus ascertains, in particular according to a predefined or predefinable parameter, at least one of the several containers as the container that is to be replaced or replenished. For example, provision can advantageously be made that the evaluation apparatus ascertains, as the one of the several containers to be replaced or replenished, the container that has the lowest fill level, so that the indicating apparatus can communicate that container to the user.

Alternatively, it is also possible for the evaluation apparatus in a treatment device configured in this fashion to ascertain at least two of the several containers for replacement or replenishment, and at the same time to specify a sequence for the filling or replacement. Provision can advantageously be made in this regard for the indicating apparatus to indicate those at least two containers, as well as the ascertained sequence, to the user. The sequence can be ascertained by the evaluation apparatus, for example, in consideration of the fill levels and/or the age of the treatment agents already present in the ascertained containers, and/or in consideration of the consumption to be expected in the future.

In a particular embodiment, the indicating apparatus comprises a display; in particular, provision can advantageously be made that the indicating apparatus indicates on the display a naturalistic or schematic image of all the containers of the treatment device, in particular in their actual physical arrangement.

The image of all the containers can be, for example, a photograph, or can be created on the basis of a photograph. Alternatively, it is also possible for the image of all the containers to be a drawing. For example, the image of all the containers can be embodied as a perspective drawing. It is also possible for the image of all the containers to be embodied as a two-dimensional depiction, for example as a plan view of the openings of the containers.

The indicating apparatus can indicate to the user the container that was ascertained by the fact that, for example, the image of the ascertained container is marked in the displayed image of all the containers. For the case in which the detected code relates to a group of treatment agents, for example a staining kit, provision can advantageously be made that the containers to be replenished or replaced are marked in treatment-agent-specific fashion in the displayed image of all containers.

In particular, provision can advantageously be made that the indicating apparatus marks in the displayed image of all containers, in chronological succession, the containers to be replaced or replenished, and at the same time respectively indicates which of the treatment agents of the group of treatment agents is to be introduced into the container whose image is marked, or which of the replacement containers of the group of treatment agents is to be used for the container whose image is marked.

No limitations exist in principle regarding the manner of marking. For example, provision can advantageously be made that the image of a container to be replaced or replenished is marked in color, as compared with the images of the containers that are not to be replaced or replenished. For example, the image of a container to be replaced or replenished can be depicted in a first color, while the images of the remaining containers that are not to be replaced or replenished are depicted in a second color different from the first color.

Alternatively or additionally, provision can also be made that the image of a container to be replaced or replenished is marked by way a brightness difference with respect to images of the containers that are not to be replaced or replenished. For example, provision can advantageously be made that the image of a container to be replaced or replenished is depicted as brighter than the images of the remaining containers that are not to be replaced or replenished.

Alternatively or additionally, provision can also be made that marking is accomplished by way of a different image sharpness. For example, the image of a container to be replaced or replenished can be depicted as sharp, while the images of the remaining containers that are not to be replaced or refilled are depicted as blurred.

Also alternatively or additionally, the marking can be accomplished by way of a flashing signal. Provision can advantageously be made in this regard, for example, that the image of a container to be replaced or replenished is depicted as flashing, while the images of the remaining containers that are not to be replaced or replenished are depicted as not flashing.

In particularly simple fashion, alternatively or additionally, marking can also be accomplished by way of an advisory symbol or several advisory symbols. For example, provision can advantageously be made that the image of a container to be replaced or replenished is marked with an arrow or another advisory symbol.

As a further marking possibility, it is possible for only an image of the container that is to be replaced or replenished to be presented on the display, while the remaining containers into which treatment agent is not to be introduced are not depicted. It is also possible to depict in the image presented on the display only those containers of a group of containers which relate to the treatment agents of a group of treatment agents, for example a staining kit. In addition, an indication can be given to the user as to which of the treatment agents of the group of treatment agents whose code was detected is to be introduced into which of the containers depicted. For example, a treatment-agent-specific advisory symbol can also be depicted on the image of each of the containers depicted.

Alternatively or in addition to communication of the ascertained container or containers via a display, the indicating apparatus can also be configured to indicate directly the container or containers that are to be replaced or replenished.

For example, provision can advantageously be made that the indicating apparatus indicates the container to be replaced or replenished by illuminating the container with light. The indicating apparatus can comprise for this at least one light source that emits a directed light beam. In addition, a beam deflection device adjustable in terms of deflection angle can be present in order to deflect the light beam onto the container to be replaced or refilled. The light source can be embodied, for example, as a laser pointer or can contain, for example, a semiconductor laser or a light-emitting diode.

For the case in which the detected code relates to a group of treatment agents, for example a staining kit, provision can advantageously be made that the indicating apparatus indicates the several containers to be replaced or replenished by illuminating the containers with light; in particular, an additional indication can be given, for example by way of the color of the light, as to which container is to be replaced with which replacement container of the group of the treatment agents whose code was detected, or which container is to be replenished using which treatment agent of the group of the treatment agents whose code was detected. It is also possible, for example, for the indicating apparatus to illuminate the several containers simultaneously while an indication is given on a display as to which of the indicated containers is to be replenished with which treatment agent, or which of the illuminated containers is to be replaced with which replacement container.

Provision can be made in this context, very generally, that the indicating apparatus indicates the containers which are to be replaced or replenished, into which the treatment agent of a group of treatment agents is to be introduced, or which are to be replaced with the replacement containers of a group of treatment agents, by illuminating them with light; and that the indicating apparatus simultaneously indicates in each case that treatment agent of the group of the treatment agents with which the currently illuminated container is to be replenished, or that replacement container of the group of treatment agents with which the currently illuminated container is to be replaced.

Alternatively or in addition to illumination and/or to indication via a display, provision can advantageously be made that the indicating apparatus indicates the container to be replaced and/or replenished by activation of a light source arranged on the container or by activation of a light source arranged in the region of the container or by activation of a light source associated with the container.

For example, a light-emitting diode can be arranged in the edge region of the opening of each container, so that the indicating apparatus can indicate, by activation of the light-emitting diode associated with the container to be replaced or refilled, which container is relevant in terms of the impending replacement or replenishment.

For the case in which the detected code relates to a group of treatment agents, for example a staining kit, provision can advantageously be made that the indicating apparatus indicates the containers to be replaced or replenished by activation of several light sources, each of the light sources respectively being arranged on one of the containers and/or arranged in the region of one of the containers and/or associated with one of the containers. Provision can advantageously be made in this context, in particular, that the indicating apparatus respectively indicates, simultaneously and additionally, that treatment agent of the group of treatment agents with which the container currently marked by means of the respective light source is to be replenished, or that replacement container of the group of treatment agents with which the container currently marked by means of the respective light source is to be replaced.

Alternatively or additionally, provision can also be made that each container of the treatment device comprises a different identification symbol, or that a different identification symbol is associated with each container; and that the indicating apparatus communicates the container that is to be replaced or replenished by reproducing the identification symbol associated with the container to be replaced or replenished. The identification symbol can be indicated, for example, on a display.

The treatment device can be configured, for example, as an automatic stainer or as a processor. The invention is not limited to such devices, however.

A particularly advantageous treatment agent product is one that contains at least one treatment agent or a group of treatment agents having an, in particular machine-readable, code that characterizes in unequivocally identifiable fashion the type of the treatment agent or the type of the group of treatment agents.

As already mentioned, the code can in particular be a QR code or a barcode, or can be stored in an RFID transponder. It is also possible, however, for a package of the treatment agent product or a container, in particular a replacement container, of the treatment agent product, to have an imprint in clear text that can be detected by the detection apparatus. The label can be, for example, a manufacturer's name and/or a common designation for a type of treatment agents. The treatment agent of the treatment agent product can be, for example, a staining agent for staining histological or cytological samples. It is also possible for the group of treatment agents of the treatment agent product to be a staining kit for staining histological or cytological samples. It is also possible for the treatment agent of the treatment agent product to be a chemical for staining a histological or cytological sample.

BRIEF DESCRIPTION OF THE DRAWING VIEWS

The subject matter of the invention is depicted schematically and by way of example in the drawings and will be described below with reference to the Figures, identical or identically functioning elements usually being labeled with the same reference characters even in different exemplifying embodiments. In the drawings.

DETAILED DESCRIPTION OF THE INVENTION

Figure 1:
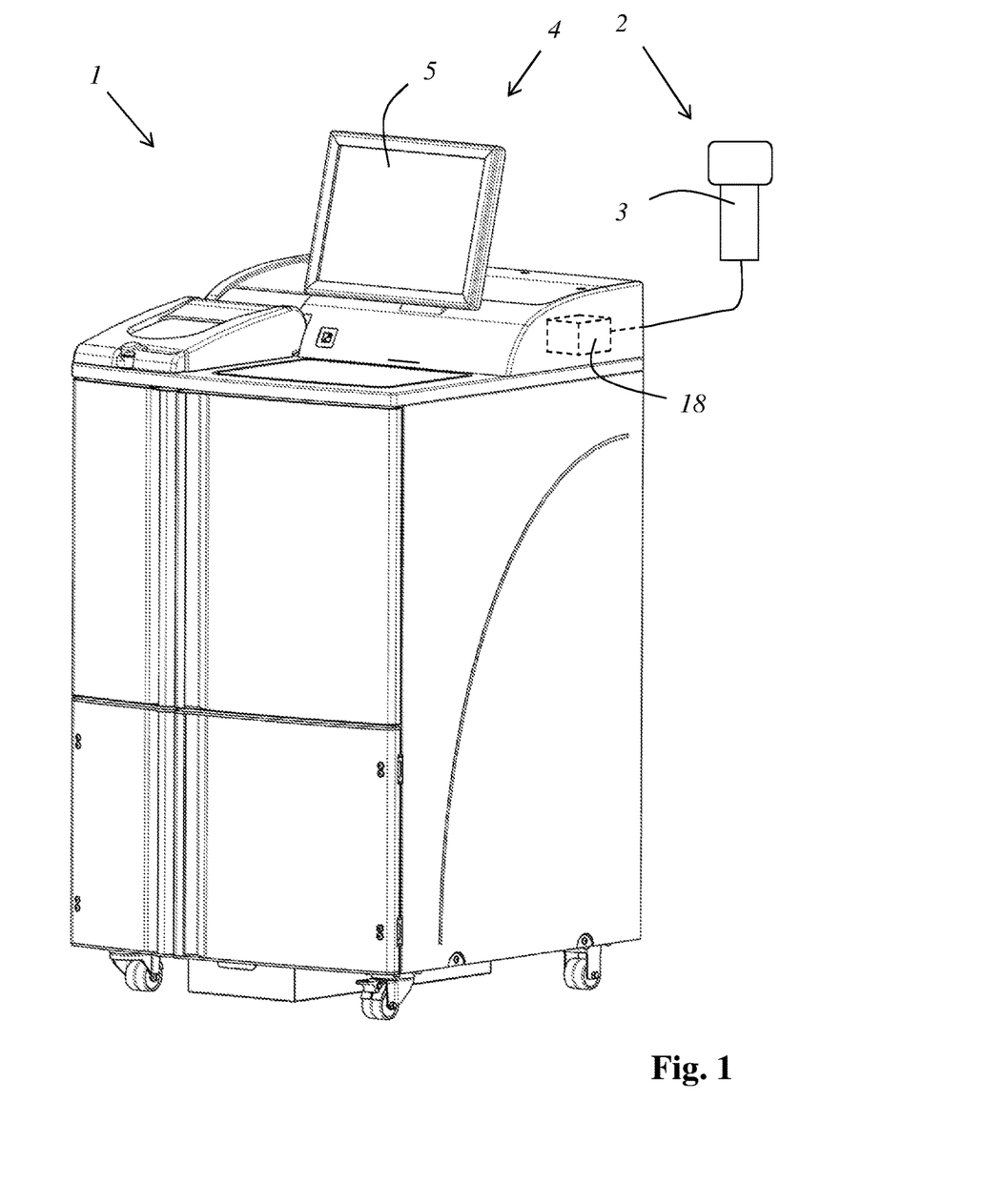
FIG. 1 shows a first exemplifying embodiment of a treatment device that is embodied as a processor.

FIG. 1 shows an exemplifying embodiment of a treatment device 1 according to the present invention for treating histological or cytological samples, which comprises a plurality of containers 6 (not visible in this Figure) for different treatment agents.

Treatment device 1 possesses a detection device 2 that is embodied as a barcode reading device 3, for detecting a code, which characterizes in unequivocally identifiable fashion the type of a treatment agent or the type of a group of treatment agents, from a package or from a replacement container of a treatment agent or of a group of treatment agents.

Treatment device 1 furthermore comprises an evaluation apparatus 18, such as a programmed computer or processor, that ascertains, in consideration of a detected code, which container 6 is to be replenished with the treatment agent the code of whose package was detected, or which container is to be replaced with a replacement container having a treatment agent the code of which, or of whose package, was detected, or which of containers 6 is to be replenished with which of the group of treatment agents whose code was detected, or which container 6 is to be replaced with which replacement container having a treatment agent of the group of treatment agents whose code was detected.

The treatment device furthermore comprises an indicating apparatus 4, namely a display 5. Indicating apparatus 4 serves to communicate to the user the ascertained container that is to be replenished or replaced, or to communicate to the user which of the ascertained containers is to be replenished with which of the group of the treatment agents whose code was detected, or is to be replaced with which replacement container of the group of treatment agents whose code was detected.

Treatment device 1 is configured as a processor for treating histological or cytological samples.

Figure 2:
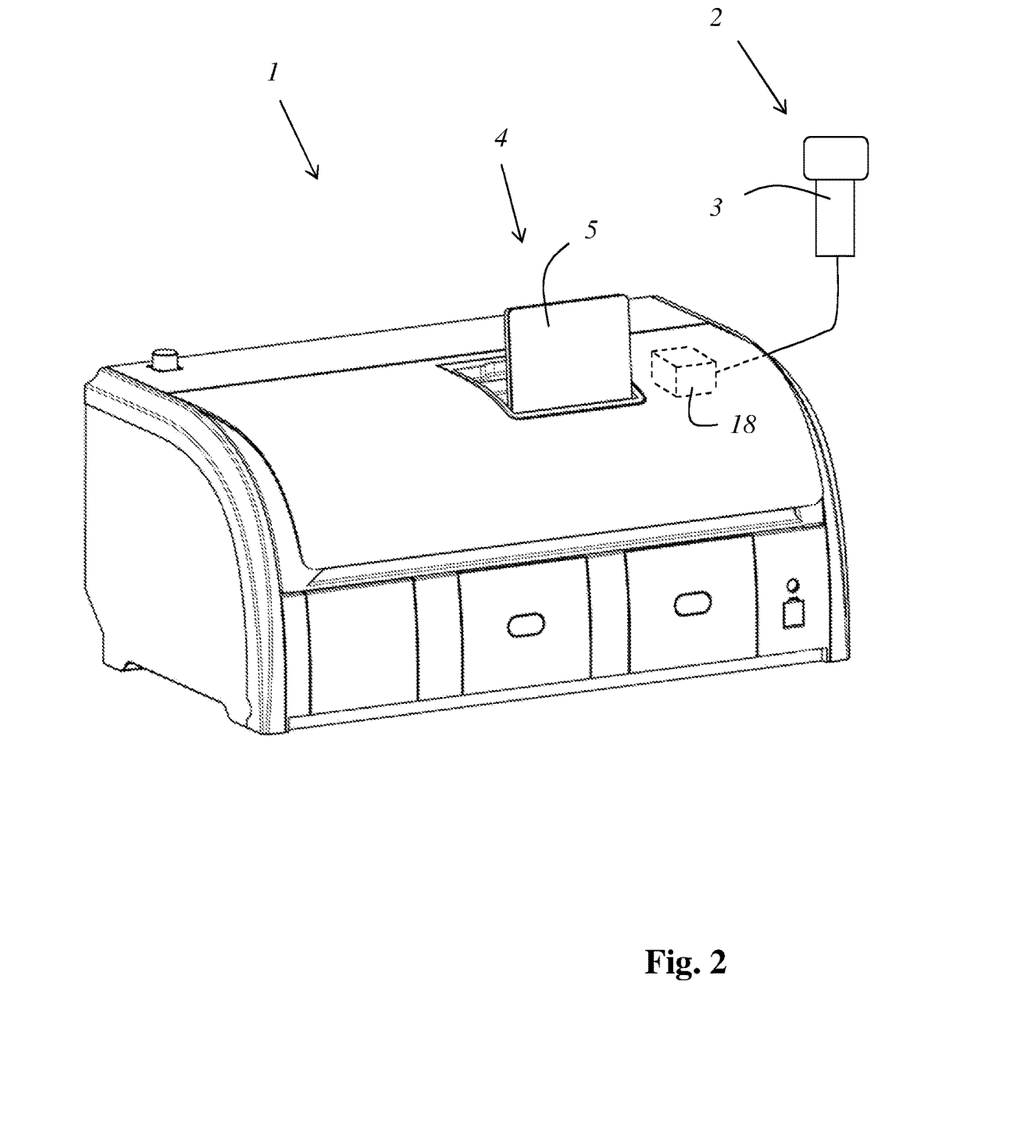
FIG. 2 shows a second exemplifying embodiment of a treatment device according to the present invention that is embodied as an automatic stainer.
Figure 3:
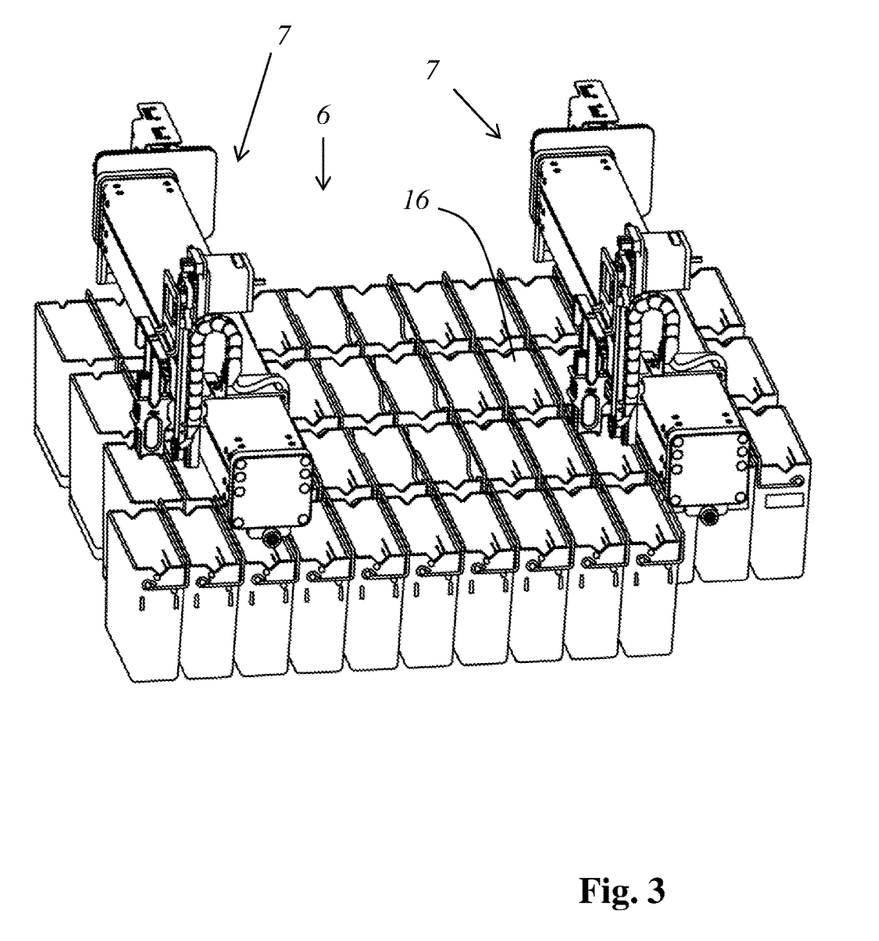
FIG. 3 is a detail view of the second exemplifying embodiment.

FIG. 2 shows a second exemplifying embodiment of a treatment device 1 according to the present invention for treating histological or cytological samples. Treatment device 1 is configured as an automatic stainer, and comprises a plurality of containers 6 for different treatment agents. Containers 6 are not visible in FIG. 2; they are shown in FIG. 3.

Treatment device 1 possesses a detection apparatus 2 which is configured as a barcode reading device 3, for detecting a code, which characterizes in unequivocally identifiable fashion the type of a treatment agent or the type of a group of treatment agents, from a package or from a replacement container of a treatment agent or of a group of treatment agents.

Treatment device 1 furthermore comprises an evaluation apparatus 18, such as a programmed computer or processor, that ascertains, in consideration of a detected code, which container 6 is to be replenished with the treatment agent the code of whose package was detected, or which container 6 is to be replaced with a replacement container having a treatment agent the code of which, or of whose package, was detected, or which of containers 6 is to be replenished with which of the group of treatment agents whose code was detected, or which container 6 is to be replaced with which replacement container having a treatment agent of the group of treatment agents whose code was detected.

Treatment device 1 furthermore comprises an indicating apparatus 4, namely a display 5. Indicating apparatus 4 serves to communicate to the user the ascertained container 6 that is to be replenished or replaced, or to communicate to the user which of the ascertained containers 6 is to be replenished with which of the group of treatment agents whose code was detected, or is to be replaced with which replacement container of the group of treatment agents whose code was detected.

FIG. 3 shows the plurality of containers 6 for different treatment agents, as well as two transport apparatuses 7 by means of which the samples to be treated are transported to the containers and from one container to another.

Figure 4:
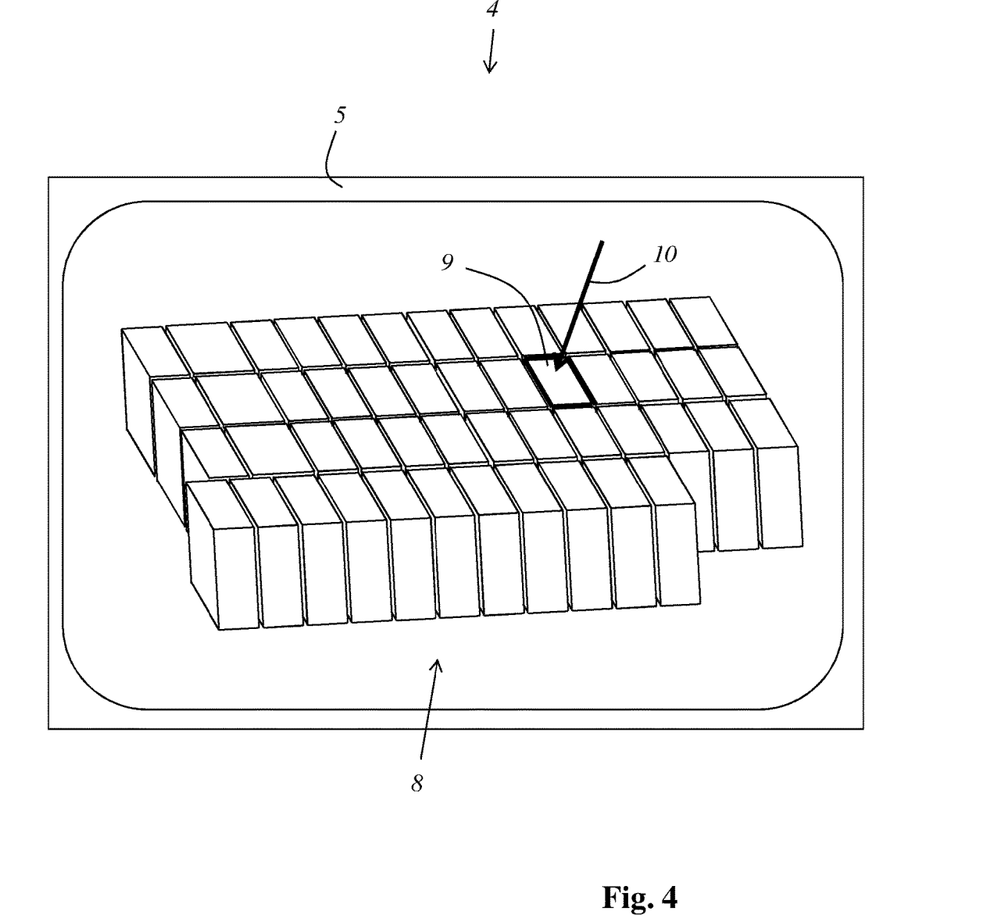
FIG. 4 shows the display of the second exemplifying embodiment.

FIG. 4 shows display 5 of indicating apparatus 4 of the second exemplifying embodiment of a treatment device 1 according to the present invention, which display communicates to the user the ascertained container 6 that is to be replenished or replaced. Concretely, display 5 indicates to the user a schematic image 8 of all the containers 6 in their actual physical arrangement. In the displayed image 8 of all containers 6, image 9 of container 16 that is to be replenished or replaced is marked with an arrow 10. In addition, image 9 of container 6 that is to be replenished or replaced is furthermore marked by a brightness difference.

Figure 5:
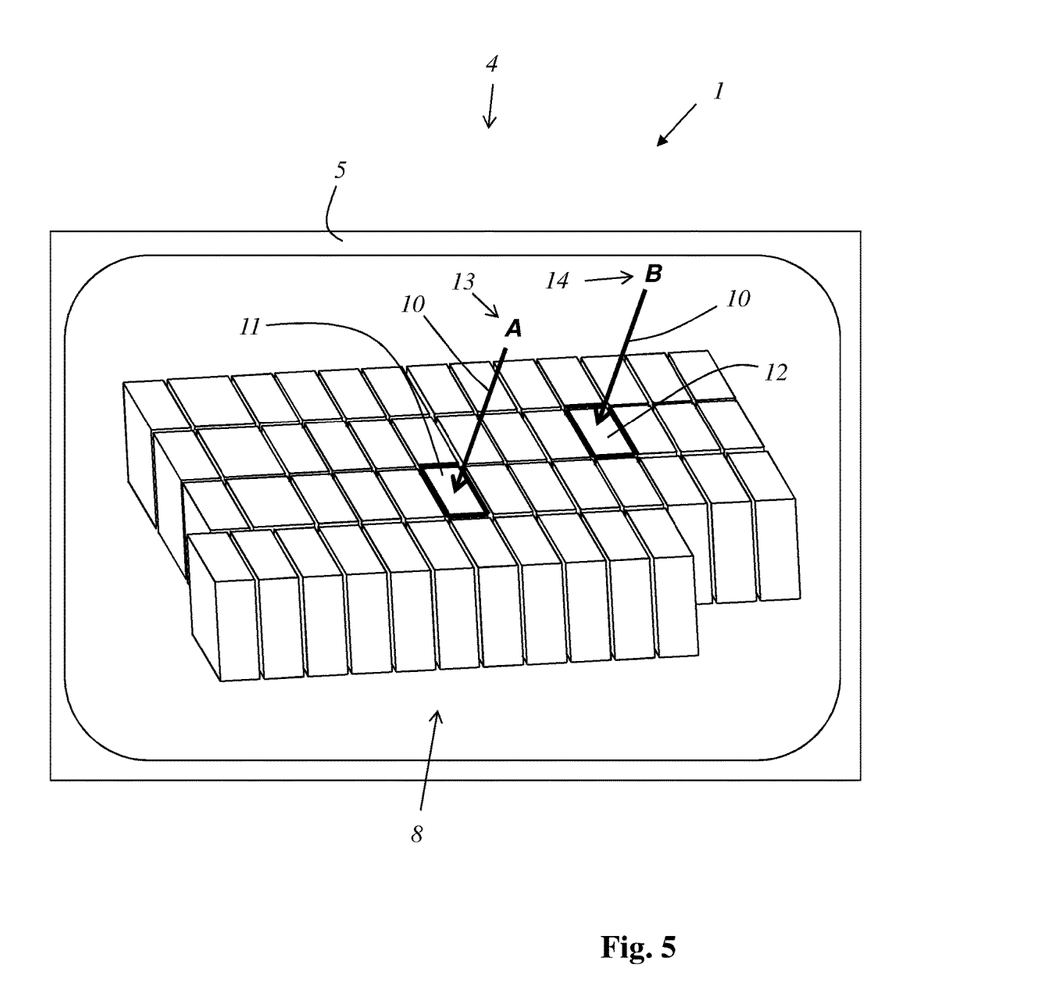
FIG. 5 shows the display of the second exemplifying embodiment for the case in which the detected code relates to a group of treatment agents.

FIG. 5 shows display 5 for the case in which the detected code relates to a group of treatment agents. In this case images 11, 12 of those containers 6 which are to be replaced or replenished are marked by means of arrows 10. At the same time, an indication is given to the user, by way of a first symbol 13 and second symbol 14, as to which of the group of treatment agents is to be introduced into which of the depicted images 11, 12 of the ascertained containers 6, or which of the replacement containers of the group of treatment agents with which of containers 6 whose images 11, 12 are marked in schematic image 8 of all containers 6.

Figure 6:
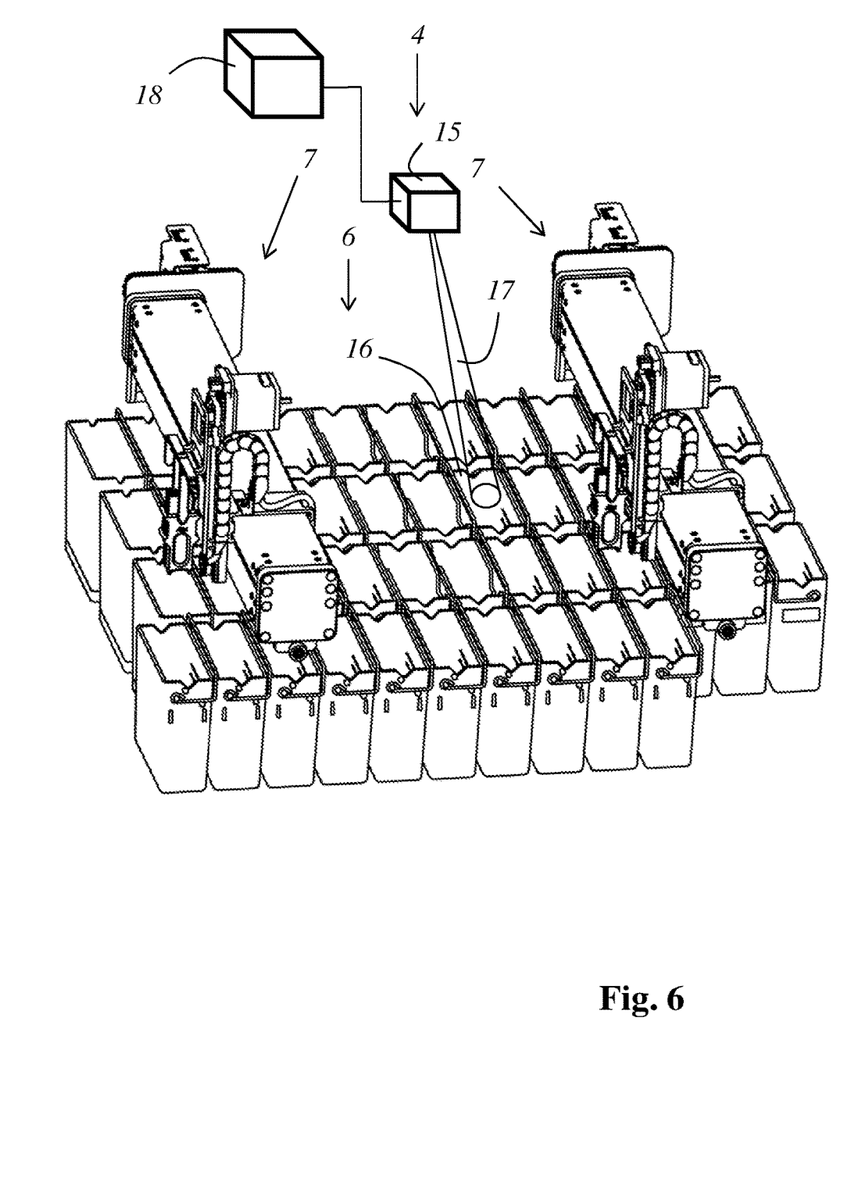
FIG. 6 is a detail view of a third exemplifying embodiment of a treatment device according to the present invention.

FIG. 6 is a detail view of a third exemplifying embodiment of a treatment device 1 according to the present invention that comprises a plurality of containers 6 as well as transport apparatuses 7.

In this third exemplifying embodiment, indicating apparatus 4 comprises a light source 15 that indicates to the user, by illumination with a light beam 17, containers 16 that are to be replaced or replenished.

PARTS LIST

1 Treatment device
2 Detection apparatus
3 Barcode reading device
4 Indicating apparatus 5 Display
6 Container
7 Transport apparatus
8 Schematic image of all containers 6
9 Image of container to be replenished or replaced
10 Arrow
11 Image
12 Image
13 First symbol
14 Second symbol
15 Light source
16 Container to be replaced or replenished
17 Light beam
18 Evaluation apparatus

What is claimed is:

1. A treatment device (1) for treating histological or cytological samples, the treatment device comprising:
a plurality of containers (6) for different treatment agents;
at least one light source operable to selectively illuminate one or more of the plurality of containers (6) for different treatment agents;
a detection apparatus (2) for detecting a code from a package or from a replacement container of a treatment agent or a group of treatment agents, wherein the code unequivocally identifies a type of the treatment agent or the group of treatment agents;
an evaluation apparatus (18) configured to ascertain, based on the detected code, which of the plurality of containers (6) is or are to be replenished or replaced; and
an indicating apparatus (4) connected to the evaluation apparatus (18), wherein the indicating apparatus (4) communicates to a user the ascertained container (6) or containers (6) that is or are to be replenished or replaced by activating the at least one light source to illuminate the ascertained container (6) or containers (6) that is or are to be replenished or replaced.

2. The treatment device (1) according to claim 1, wherein the evaluation apparatus (18) comprises a memory.

3. The treatment device (1) according to claim 2, wherein the evaluation apparatus (18) is configured to store in the memory
a. which type of treatment agent is located in which of the plurality
b. a plurality of types of treatment agents and a separate treatment agent identifier associated with each of the plurality of types of treatment agents;
c. the type of treatment agent present in at least one of the plurality of containers (6) and a separate treatment agent identifier associated therewith; and/or
d. the type of treatment agent present in at least one of the plurality of container (6) and a container identifier associated therewith.

4. The treatment device (1) according to claim 2, wherein the evaluation apparatus (18) is configured to:
a. associate with the detected code at least one treatment agent identifier from a plurality of previously stored treatment agent identifiers; and/or
b. associate with the detected code at least one of a plurality of previously stored treatment agent identifiers and then read out from the memory, on the basis of the associated treatment agent identifier, a container identifier stored in the memory, the container identifier corresponding to one of the plurality of containers (6) which contains the type of treatment agent corresponding to the associated treatment agent identifier.

5. The treatment device (1) according to claim 1, wherein the detection apparatus (2) is configured to detect, as the code, a barcode and/or a QR code and/or a machine-readable imprint and/or a transponder code and/or an RFID transponder code.

6. The treatment device (1) according to claim 1, wherein several among the plurality of containers (6) are present for the same treatment agent.

7. The treatment device (1) according to claim 6, wherein the evaluation apparatus (18) is configured to ascertain at least one of the several containers (6) as the container (6) to be replaced or replenished.

8. The treatment device (1) according to claim 7, wherein the evaluation apparatus (18) is configured to ascertain, as the container to be replaced or replenished, that one of the several containers (6) which has a lowest fill level of the treatment agent; and the indicating apparatus (4) communicates that one container (6) of the several containers (6) to the user.

9. The treatment device (1) according to claim 6, wherein the evaluation apparatus (18) is configured to ascertain a sequence for the filling or replacement of at least two of the several containers (6), and the indicating apparatus (4) indicates those at least two containers, as well as the sequence, to the user.

10. The treatment device (1) according to claim 9, wherein the evaluation apparatus (18) is configured to ascertain the sequence in consideration of respective fill levels and/or respective ages of the treatment agents already present in the containers (6), and/or in consideration of an expected consumption of the treatment agents already present in the containers (6).

11. The treatment device (1) according to claim 1, wherein the indicating apparatus (4) directly indicates the container (6) or containers (6) that are to be replaced or replenished.

12. The treatment device (1) according to claim 1, wherein
a. the indicating apparatus (4) activates the at least one light source to indicate, by sequential illumination of a respective one of the plurality of containers (6) with light, which of the containers (6) is to be replenished with which of the group of treatment agents whose code was detected, or which container (6) is to be replaced with which replacement container having treatment agent of the group of treatment agents whose code was detected; or
b. the indicating apparatus (4) activates the at least one light source to indicate the containers (6) which are to be replaced or replenished, into which the treatment agent of a group of treatment agents is to be introduced, or which are to be replaced with the replacement containers of a group of treatment agents, by illumination with light; and the indicating apparatus (4) activates the at least one light source to simultaneously respectively indicate a corresponding one of the treatment agents of the group of treatment agents with which the currently illuminated container (6) is to be replaced, or a corresponding one of the replacement containers of the group of treatment agents with which the currently illuminated container (6) is to be replaced.

13. The treatment device (1) according to claim 1, wherein the at least one light source includes a respective light source for each of the plurality of containers (6) wherein the respective light source is arranged on the corresponding container (6), is arranged in the region of the corresponding container (6), or is associated with the corresponding container (6).

14. The treatment device (1) according to claim 1, wherein the treatment device (1) is an automatic stainer or a processor.

15. A treatment device (1) for treating histological or cytological samples, the treatment device comprising:
- a plurality of containers (6) for different treatment agents;
- a detection apparatus (2) for detecting a code from a package or from a replacement container of a treatment agent or a group of treatment agents, wherein the code unequivocally identifies a type of the treatment agent or the group of treatment agents;
- an evaluation apparatus (18) configured to ascertain, based on the detected code, which of the plurality of containers (6) is or are to be replenished or replaced; and
- an indicating apparatus (4) comprising a display (5), the indicating apparatus being connected to the evaluation apparatus (18), wherein the indicating apparatus (4) communicates to a user the ascertained container (6) or containers (6) that is or are to be replenished or replaced by displaying on the display (5) a schematic image of the plurality of containers (6) in their actual physical arrangement, wherein:
  a. an image of each ascertained container (6) to be replenished or replaced is marked in the displayed image of the plurality of containers (6); or
  b. an image of each ascertained container (6) to be replenished or replaced is marked in treatment-agent-specific fashion in the displayed image of the plurality of containers (6); or
  c. the indicating apparatus (4) marks in the displayed image of the plurality of containers (6), in chronological succession, an image of each containers (6) to be replaced or replenished, and at the same time respectively indicates which of the treatment agents of the group of treatment agents is or are to be introduced into each container (6) whose image is marked, or which of the replacement containers is to be used for each container (6) whose image is marked.

16. The treatment device (1) according to claim 15, wherein the image of the plurality of containers (6) is a photograph or a drawing.

17. The treatment device (1) according to claim 15, wherein the image of each container (6) to be replaced or replenished is, with respect to images of the containers (6) that are not to be replaced or replenished,
   a. marked by way of a color difference, and/or
   b. marked by way of a brightness difference, and/or
   c. marked by way of a different image sharpness, and/or
   d. marked by way of a flashing signal, and/or
   e. marked by way of an advisory symbol, and/or
   f. displayed, while the containers (6) that are not to be replaced or replenished are blanked out.

18. A treatment device (1) for treating histological or cytological samples, the treatment device comprising:
- a plurality of containers (6) for different treatment agents;
- a detection apparatus (2) for detecting a code from a package or from a replacement container of a treatment agent or a group of treatment agents, wherein the code unequivocally identifies a type of the treatment agent or the group of treatment agents;
- an evaluation apparatus (18) configured to ascertain, based on the detected code, which of the plurality of containers (6) is or are to be replenished or replaced; and
- an indicating apparatus (4) comprising a display (5), the indicating apparatus being connected to the evaluation apparatus (18), wherein the indicating apparatus (4) communicates to a user the ascertained container (6) or containers (6) that is or are to be replenished or replaced; wherein
  a. each container (6) comprises a different identification symbol; or a different identification symbol is associated with each container (6); and
  b. the indicating apparatus (4) communicates the container (6) that is to be replaced or replenished by reproducing the identification symbol of such container (6) on the display (5).

* * * * *